United States Patent [19]

Furukawa et al.

[11] Patent Number: 4,857,524

[45] Date of Patent: Aug. 15, 1989

[54] THIAZOLIDINE COMPOUNDS AND THERAPEUTIC METHOD

[75] Inventors: Sunao Furukawa; Tadashi Yoshimoto, both of Nagasaki; Yukiyoshi Ajisawa, Okaya; Seiichi Ikeguchi, Nagano; Yukihiko Kinoshita, Matsumoto, all of Japan

[73] Assignee: Kissei Pharmaceutical Co., Ltd., Matsumoto, Japan

[21] Appl. No.: 227,864

[22] Filed: Aug. 3, 1988

[30] Foreign Application Priority Data

Aug. 8, 1987 [JP] Japan .................................. 62-198380
Mar. 7, 1988 [JP] Japan .................................. 63-53224

[51] Int. Cl.$^4$ ................... A01N 31/425; A01N 31/54; C07D 417/06
[52] U.S. Cl. ................................ 514/227.5; 514/236.8; 514/318; 514/319; 514/320; 514/342; 514/365; 544/58.4; 544/131; 544/133; 546/193; 546/205; 546/206; 546/209; 546/280; 548/200
[58] Field of Search ...................... 544/58.4, 131, 133; 546/193, 205, 206, 209, 280; 548/200; 514/227.5, 236.8, 318, 319, 326

[56] References Cited

U.S. PATENT DOCUMENTS 4,628,101 12/1986 Camaggi et al. ..................... 548/200

Primary Examiner—Robert W. Ramsuer
Attorney, Agent, or Firm—Depaoli & O'Brien

[57] ABSTRACT

In one embodiment this invention provides novel thiazolidine compounds, such as 3-[R-(-)-3-benzyloxycarbonylthiazolidine-4-carbonyl]thiazolidine corresponding to the formula:

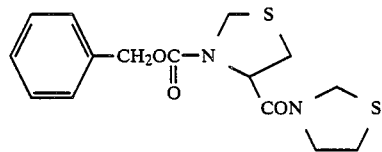

An invention thiazolidine compound exhibits prolyl endopeplidase inhibitory activity, and has utility as a therapeutic agent for the treatment of dementia and amnesia disorders.

27 Claims, No Drawings

THIAZOLIDINE COMPOUNDS AND THERAPEUTIC METHOD

FIELD OF THE INVENTION

The present invention relates to novel thiazolidine compounds being useful as therapeutical agents.

More particularly, the present invention relates to thiazolidine compounds represented by the general formula:

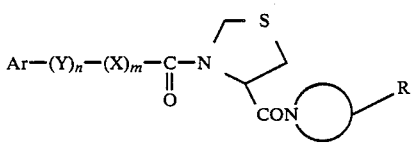

wherein Ar is a phenyl, naphthyl or pyridyl group; Y is a saturated or olefinically unsaturated alkylene group having 1–5 carbon atoms; n is an integer having a value of zero or 1,

is a 5- or 6-membered saturated heterocyclic group; X is an oxygen atom; m is an integer with a value of zero or 1; R is hydrogen or an alkoxycarbonyl group having 2–6 carbon atoms; and pharmaceutically acceptable salts thereof; which possess an inhibitory activity for a prolyl endopeptidase (Post-proline cleaving enzyme), and thus which are useful for the treatment of diseases such as dementia and amnesia.

BACKGROUND OF THE INVENTION

Cerebral vasodilators and cerebral excitometabolic agents up to the present time have been employed as therapeutical agents for the treatment of diseases such as dementia and amnesia. It has been reported that these agents are effective for the treatment of dementia caused by cerebrovascular disorders. However, these agents do not show a sufficient effect for the treatment of dementia due to causes other than cerebrovascular disorders.

Prolyl endopeptidase is well known as an enzyme which acts on biologically active peptides and substrates to cleave specifically the carboxyl site in proline moiety.

The prolyl endopeptidase decomposes vasopressin and thyrotropin releasing hormone which are closely related to a memory mechanism, and therefore, a relationship of the inhibitory effect of prolyl endopeptidase and amnesia has been the subject of long term studies. As a result, it is suggested that inhibitors for the prolyl endopeptidase are useful for the treatment of dementia and amnesia (Seikagaku Vol. 55, No. 8, page 831, 1983).

With regard to inhibitors of prolyl endopeptidase, Japanese patent application (OPI) No. 188317/85 (The term "OPI" as used herein refers to an unexamined Japanese patent application) discloses the compound represented by the formula:

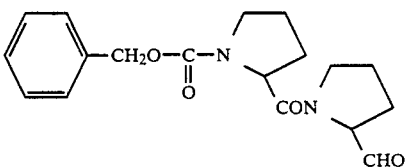

With respect to thiazolidine compounds having structures related to the compounds of the present invention, several compounds have been reported in the literature. For example, the compound represented by the formula:

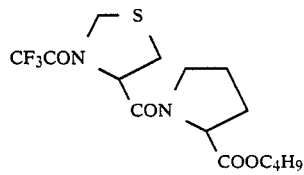

is disclosed in Chemical Abstracts, Vol. 86, No. 17, 117082v (1977), and has been prepared to study fragments in Mass spectrum. The compound represented by the formula:

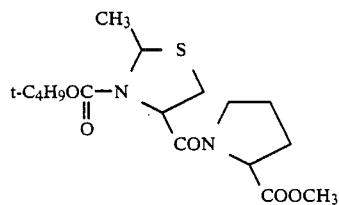

is disclosed in Chemical Abstracts, Vol. 105, No. 25, 227322s (1986), and is an intermediate for the preparation of agents for treatment of liver disorders.

In Chemical Abstracts, Vol. 95, No. 19, 169173f (1981), Vol. 96, No. 15, 123303r (1982), the following thiazolidine compounds having hypotensive activities are disclosed:

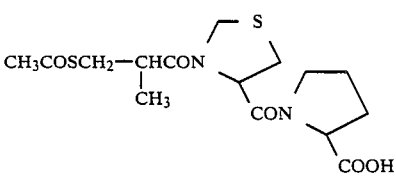

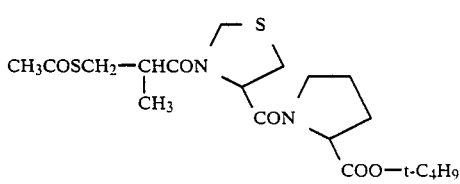

-continued $$CH_3COSCH_2CH_2CON\underset{\underset{COO-t-C_4H_9}{|}}{\overset{\overset{\text{HO}}{\underset{|}{\text{C}_6H_4}}}{C}}H-CH_2-S-CH(CON<)-CH_2-CH_2$$
(thiazolidine ring with pyrrolidine CON substituent)

However, it is not disclosed that those compounds have an inhibitory effect on prolyl endopeptidase, and that they are useful as therapeutical agents for the treatment of dementia and amnesia. Further, no thiazolidine compound of the present invention type structure as yet has been reported to have an inhibitory activity for prolyl endopeptidase enzyme.

SUMMARY OF THE INVENTION

An object of the present invention is to provide novel thiazolidine compounds and pharmaceutically acceptable salts thereof which exhibit an inhibitory effect on prolyl endopeptidase.

Another object of the present invention is to provide novel thiazolidine compounds and pharmaceutically salts thereof which are useful as therapeutical agents for the treatment of dementia and amnesia.

Other objects, features and advantages of the present invention will be apparent from the following description of the invention.

DETAILED DESCRIPTION OF THE INVENTION

One or more objects of the present invention are accomplished by the provision of novel thiazolidine compounds of the general formula (I):

$$Ar-(Y)_n-(X)_m-\underset{O}{\overset{\|}{C}}-N\underset{CON}{\overset{S}{\diagup}}\diagdown R \qquad (I)$$

where Ar is a phenyl, naphthyl or pyridyl group; Y is a saturated or olefinically unsaturated alkylene group having 1–5 carbon atoms; n is an integer with a value of zero or 1;

$$-N\bigcirc$$

is a 5- or 6-membered saturated heterocyclic group; X is an oxygen atom; m is an integer with a value of zero or 1; R is hydrogen or an alkoxycarbonyl group having 2–6 carbon atoms; and pharmaceutically acceptable salts thereof.

The term "alkoxycarbonyl" as used herein means alkoxycarbonyl group having 2 to 6 carbon atoms.

The moiety $$-N\bigcirc$$

as used herein means pyrrolidine thiazolidine, piperidine, morpholine and thiomorpholine.

The term "alkoxy" as used herein means a straight- or branched-alkoxy group having 1 to 5 carbon atoms.

The thiazolidine compounds of the present invention and pharmaceutically acceptable salts thereof exhibit an inhibitory effect on prolyl endopeptidase, and thus are useful as therapeutical agents for the treatment of dementia and amnesia.

The thiazolidine compounds (I) of the present invention are novel compounds, and can be prepared in one method by reacting a compound represented by the general formula (II):

$$Ar-(Y)_n-(X)_m-\underset{O}{\overset{\|}{C}}-N\underset{COOH}{\overset{S}{\diagup}} \qquad (II)$$

where Ar, Y, n, X and m have the same meanings as defined above, or a reactive functional derivative thereof, with a compound represented by the general formula (III):

$$HN\bigcirc-R \qquad (III)$$

wherein $$-N\bigcirc$$

and R have the same meanings as defined above.

The compounds (II) and (III) used as starting materials are known compounds and commercially available. They can be also prepared by methods disclosed in the chemical literature.

The production of the compounds of the general formula (I) of the present invention can be achieved by using a peptide-synthesis procedure. For example, when the carboxylic acid compound of the general formula (II) is employed as a starting material to prepare the invention compounds of the general formula (I), the process can be conducted in the presence of a condensing agent used in peptide synthesis, such as N,N'-dicyclohexylcarbodiimide.

Examples of reactive functional derivatives of the compounds (II) useful as starting materials include acid halides, acid anhydrides, mixed acid anhydrides and active esters.

The thiazolidine compounds of the present invention contain one or two asymmetric carbon atoms including one in the thiazolidine-4-carboxylic acid moiety. Various stereoisomers of the thiazolidine compounds of the present invention exist depending upon the configuration of each asymmetric carbon atoms. Configuraof substituents on each asymmetric carbon atom may be of R- or S-configuration, and a racemic mixture of S- and R-configurations can be employed in the present invention. Optically active compounds of the general formula (I) of the present invention can be prepared by using optically active starting materials.

Of the thiazolidine compounds represented by the general formula (I) of the present invention, preferred compounds are those in which Y is methylene and m and n are one, respectively. The most preferred compound on the basis of enzyme inhibitory activity is 3-[R-(—)-3-benzyloxycarbonylthiazolidine-4-carbonyl]-thiazolidine.

The thiazolidine compounds represented by the general formula (I) of the present invention can be converted according to conventional methods into pharmaceutically acceptable salts thereof. Examples of such pharmaceutically acceptable salts include pharmaceutically acceptable inorganic or organic acid salts such as hydrochloric acid salt, sulfuric acid salt, p-toluenesulfonic acid salt, acetic acid salt, citric acid salt, tartaric acid salt, succinic acid salt, fumaric acid salt, and the like. These salts have an inhibitory effect as high as the corresponding compound having a free amino group.

In another embodiment this invention provides a method of treatment for dementia or amnesia which comprises administering a prescribed dosage to a human patient of a therapeutic agent corresponding to the formula:

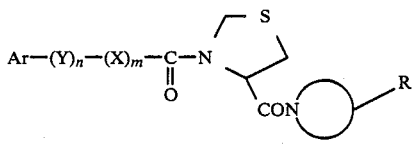

wherein Ar is a phenyl, naphthyl or pyridyl group; Y is a saturated or olefinically unsaturated alkylene group having 1–5 carbon atoms; n is an integer with a value of zero or 1;

is a 5- or 6-membered saturated heterocyclic group; X is an oxygen atom; m is an integer with a value of zero or 1; R is hydrogen or an alkoxycarbonyl group having 2–6 carbon atoms; or pharmaceutically acceptable salt thereof.

The thiazolidine compounds represented by the general formula (I) of the present invention exhibit an inhibitory effect on prolyl endopeptidase. For example, the thiazolidine compounds of the general formula (I) produce a 50% inhibition in an in vitro experiment using prolyl endopeptidase from bovine brain at $7 \times 10^{-5}$ to $3 \times 10^{-10}$ molar concentrations.

Specifically, 3-[(R)-(—)-3-benzyloxycarbonyl]-thiazolidine-4-carbonyl]thiazolidine produces a 50% inhibition at $2.6 \times 10^{-10}$ molar concentration. Thus, the thiazolidine compounds of the present invention possess an inhibitory activity for prolyl endopeptidase, and are useful as therapeutic agents with a low toxicity for the treatment of dementia and amnesia.

The thiazolidine compounds represented by the general formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The thiazolidine compounds and the pharmaceutically acceptable salts of the general formula (I) of the present invention can be administered in various dosage forms depending upon the intended therapy. Typical dosage forms which can be used are tablets, pills, powders, liquid preparations, suspensions, emulsions, granules, capsules, suppositories, and injectable preparations.

When molding a pharmaceutical composition into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugar-coated tablets, gelatin-coated tablets, film-coated tablets, or tablets coated with two or more layers.

When a pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution The therapeutic agent may further contain ordinary dissolving aids, buffers, pain-alleviating agents, and preservatives, and optionally, coloring agents fragrances, flavors, sweeteners, and other pharmacologically active agents which are known in the art.

The dosage of the amino acid derivatives of this invention may be in the range from about 50 mg to 1000 mg for adult human by oral administration per day, or from about 1 mg to 500 mg for adult human by parenteral administration per day in multiple doses depending upon the type of disease, the severity of condition to be treated, and the like.

REFERENCE EXAMPLE 1

(R)-(—)-3-Benzyloxycarbonylthiazolidine-4-carboxylic acid

To a solution of 2.66 g of (R)-(—)-thiazolidine-4-carboxylic acid in 10 ml of a 2N-aqueous sodium hydroxide solution were added 4.1 g of benzyloxycarbonyl chloride and 15 ml of a 2N-aqueous sodium hydroxide solution with stirring under ice-cooling at the same time, and then the mixture was stirred for 2 hours at room temperature. The reaction mixture was washed with diethyl ether. The reaction mixture was then acidified by adding hydrochloric acid under ice-cooling. The mixture was allowed to stand for 30 minutes, and then the mixture was extracted with ethyl acetate. The organic layer was washed with a saturated sodium chloride aqueous solution, dried over anhydrous sodium sulfate, and evaporated under reduced pressure to obtain 4.14 g of (R)-(—)-3-benzyloxycarbonylthiazolidine- 4-carboxylic acid as a colorless clear viscous oil. The oily substance was allowed to stand under cooling to form a solid, and the solid was recrystallized from diethyl ether-petroleum ether to obtain a pure (R)-(−)-3-benzyloxycarbonylthiazolidine-4-carboxylic acid.

melting point: 58°–63° C.
$[\alpha]_D^{22} = -97.5°$ (c=1, ethyl acetate)
MS: m/z=267 (M+)
IR (KBr): νco 1742, 1664 cm$^{-1}$
NMR (CDCl$_3$) δ: 3.30(d, 2H), 4.58(AB-q, 2H), 4.90(br-s, 1H), 5.18(s, 2H), 7.34(s, 5H), 8.50(s, 1H)
elemental analysis as C$_{12}$H$_{13}$NO$_4$S

|        | C %   | H %  | N %  |
|--------|-------|------|------|
| Calcd. | 53.93 | 4.90 | 5.24 |
| Found  | 53.86 | 4.87 | 5.19 |

REFERENCE EXAMPLE 2

(R)-(−)-3-(3-Phenylpropionyl)thiazolidine-4-carboxylic acid

To a solution of 2.66 g of (R)-(−)-thiazolidine-4-carboxylic acid in 10 ml of a 2N sodium hydroxide aqueous solution were added 5.5 g of 3-phenylpropionyl chloride and 15 ml of a 2N-sodium hydroxide aqueous solution with stirring under cooling at the same time. After adding, the mixture was stirred for 2 hours at room temperature, and then the reaction mixture was washed with diethyl ether. The mixture was acidified by adding hydrochloric acid. The acidic mixture was allowed to stand for 30 minutes, and extracted with ethyl acetate. The organic layer was washed with a saturated sodium chloride aqueous solution, dried over anhydrous sodium sulfate, and evaporated under reduced pressure. The residue was recrystallized from ethyl acetate to obtain 4.06 g of (R)-(−)-3-(3-phenylpropionyl)thiazolidine-4-carboxylic acid. (yield: 76.5%)

melting point: 93°–95° C.
IR (KBr): νco 1730, 1596 cm$^{-1}$
MS (EI): C$_{13}$H$_{15}$O$_3$NS=265.28 m/z 265(M+), 248, 220, 174, 160, 150, 91
$[\alpha]_D^{20} = -97.5°$ (c=0.5, diethyl ether)
elemental analysis as C$_{13}$H$_{15}$O$_3$NS

|        | C %   | H %  | N %  | S %   |
|--------|-------|------|------|-------|
| Calcd. | 58.86 | 5.70 | 5.28 | 12.06 |
| Found  | 58.71 | 5.71 | 5.33 | 12.05 |

REFERENCE EXAMPLE 3

The following compounds were prepared in a similar manner to that described in Reference Example 1 by using a proper starting material.

(R)-(−)-3-(4-Phenylbutanoyl)thiazolidine-4-carboxylic acid melting point: 87°–90° C.
IR (KBr): νco 1715, 1610 cm$^{-1}$
MS (EI): C$_{14}$H$_{17}$O$_3$NS=279.30 m/z 279 (M+), 235, 188, 175, 133, 91
$[\alpha]_D^{22} = -90.8°$ (c=0.46, ethyl acetate)
elemental analysis as C$_{14}$H$_{17}$O$_3$NS

|        | C %   | H %  | N %  | S %   |
|--------|-------|------|------|-------|
| Calcd. | 60.20 | 6.14 | 5.02 | 11.45 |
| Found  | 59.99 | 6.13 | 4.97 | 11.37 |

(R)-(−)-3-Phenylacetylthiazolidine-4-carboxylic acid melting point: 136°–138° C.
IR (KBr): νco 1710, 1590 cm$^{-1}$
$[\alpha]_D^{23} = -115.4°$ (c=1.0, methanol)
elemental analysis as C$_{12}$H$_{13}$O$_3$NS

|        | C %   | H %  | N %  | S %   |
|--------|-------|------|------|-------|
| Calcd. | 57.37 | 5.22 | 5.58 | 12.74 |
| Found  | 57.51 | 5.27 | 5.45 | 12.68 |

(R)-(−)-3-Cinnamoylthiazolidine-4-carboxylic acid melting point: 184°–186° C.
IR (KBr): νco 1740, 1650 cm$^{-1}$
$[\alpha]_D^{24\ 24} = -129.6°$ (c=1.0, methanol)
elemental analysis as C$_{13}$H$_{13}$O$_3$NS

|        | C %   | H %  | N %  | S %   |
|--------|-------|------|------|-------|
| Calcd. | 59.31 | 4.98 | 5.32 | 12.16 |
| Found  | 59.21 | 5.26 | 5.00 | 11.74 |

(R)-(−)-3-(1-Naphthylacetyl)thiazolidine-4-carboxylic acid melting point: 146°–148° C.
IR (KBr): νco 1735, 1610 cm$^{-1}$
MS(EI): C$_{16}$H$_{15}$O$_3$NS=301.30 m/z 301(M+), 229, 168, 141, 132, 88
$[\alpha]_D^{20} = -86.7°$ (c=0.75, dimethylsulfoxide)
elemental analysis as C$_{16}$H$_{15}$O$_3$NS

|        | C %   | H %  | N %  | S %   |
|--------|-------|------|------|-------|
| Calcd. | 63.78 | 5.02 | 4.65 | 10.62 |
| Found  | 53.89 | 5.28 | 4.65 | 10.58 |

EXAMPLE 1

3-[(R)-(−)-3-Benzyloxycarbonylthiazolidine-4-carbonyl]thiazolidine (Compound A)

To a solution of 2.67 g of (R)-(−)-3-benzyloxycarbonylthiazoline-4-carboxylic acid and 1.15 g of N-hydroxysuccinimide in 20 ml of dioxane was added 5 ml of dioxane containing 2.06 g of N,N'-dicyclohexylcarbodiimide with stirring under cooling. The mixture was allowed to stand overnight under cooling, and precipitates were filtrated off. The filtrate was evaporated under reduced pressure, and the residue was dissolved in 15 ml of dimethoxyethane. To the solution was added 0.89 g of thiazolidine with stirring under cooling, and the mixture was allowed to stand overnight. The reaction mixture was evaporated under reduced pressure, and to the residue was added 5 ml of water. The mixture was stirred for 30 minutes, and then extracted with ethyl acetate. The organic layer was washed successively with a 1N hydrochloric acid, a 5% aqueous sodium bicarbonate solution and a saturated sodium chloride aqueous solution, dried over anhydrous magnesium sulfate, and evaporated under reduced pressure. The residue was purified by silica gel column chromatography to obtain 3-[(R)-(−)-3-benzyloxycarbonylthiazolidine-4-carbonyl]thiazolidine as colorless needles. (developing solvent:ethyl acetate/benzene=6/4)

melting point: 73°–75° C.
$[\alpha]_D^{20} = -83.0°$ (c=1, ethyl acetate)
MS: m/z=338 (M+)
IR (KBr): νco 1701, 1640 cm$^{-1}$
NMR (CDCl$_3$) δ: 2.8–3.2(br-m, 2H), 3.25(m, 2H), 3.4–4.0(br-m, 2H), 4.5–5.0(m, 5H), 5.13(s, 2H), 7.34(s, 5H)
elemental analysis as C$_{15}$H$_{18}$N$_2$O$_3$S$_2$

|  | C % | H % | N % |
|---|---|---|---|
| Calcd. | 53.25 | 5.36 | 8.28 |
| Found | 53.61 | 5.55 | 8.01 |

EXAMPLE 2

The following compounds were prepared in a similar manner to that described in Example 1 by using a corresponding starting material.

(S)-(−)-N-[(R)-(−)-3-Benzyloxycarbonylthiazolidine-4-carbonyl]pyrrolidine-2-carboxylic acid methyl ester (Compound B)

oil
MS(EI): C$_{18}$H$_{22}$N$_2$O$_5$S=378.447 m/z 378(M+), 184, 146, 91

N-[(R)-(−)-3-Benzyloxycarbonylthiazolidine-4-carbonyl]thiazolidine (Compound C)

melting point: 88°–90° C.
MS(EI): C$_{16}$H$_{20}$N$_2$O$_3$S=320.411 m/z 320(M+), 185, 126, 91
$[\alpha]_D^{20} = -90.0°$ (c=1, ethyl acetate)
elemental analysis as C$_{16}$H$_{20}$N$_2$O$_3$S

|  | C % | H % | N % | S % |
|---|---|---|---|---|
| Calcd. | 59.99 | 6.29 | 8.75 | 9.99 |
| Found | 60.08 | 6.35 | 8.70 | 10.11 |

N-[(R)-(−)-3-Benzyloxycarbonylthiazolidine-4-carbonyl]piperidine (Compound D)

melting point: 90°–92° C.
MS(EI): C$_{17}$H$_{22}$N$_2$O$_3$S=334.438 m/z 334(M+), 199, 140, 91
elemental analysis as C$_{17}$H$_{22}$N$_2$O$_3$S

|  | C % | H % | N % | S % |
|---|---|---|---|---|
| Calcd. | 61.06 | 6.63 | 8.38 | 9.57 |
| Found | 60.99 | 6.63 | 8.33 | 9.60 |

N-[(R)-(−)-3-Benzyloxycarbonylthiazolidine-4-carbonyl]morpholine (Compound E)

melting point: 114°–115° C.
MS(EI) : C$_{16}$H$_{20}$N$_2$O$_4$S=336.410 m/z 336(M+), 201, 142, 91
elemental analysis as C$_{16}$H$_{20}$N$_2$O$_4$S

|  | C % | H % | N % | S % |
|---|---|---|---|---|
| Calcd. | 57.13 | 5.99 | 8.33 | 9.51 |
| Found | 57.31 | 5.98 | 8.30 | 9.48 |

N-[(R)-(−)-3-Benzyloxycarbonylthiazolidine-4-carbonyl]thiomorpholine (Compound F)

melting point: 120°–123° C.
MS(EI) : C$_{16}$H$_{20}$N$_2$O$_3$S$_2$=352.475 m/z 352(M+), 279, 217, 157, 91
$[\alpha]_D^{20} = -103.43°$ (c=1, ethyl acetate)
elemental analysis as C$_{16}$H$_{20}$N$_2$O$_3$S$_2$

|  | C % | H % | N % | S % |
|---|---|---|---|---|
| Calcd. | 54.54 | 5.72 | 7.95 | 18.16 |
| Found | 54.38 | 5.64 | 7.87 | 18.34 |

(R)-(−)-3-[(R)-(−)-3-Benzyloxycarbonylthiazolidine-4-carbonyl]thiazolidine-4-carboxylic acid methyl ester (Compound G)

melting point: 102°–104° C.
MS(EI): C$_{17}$H$_{20}$N$_2$O$_5$S$_2$=396.484 m/z 396(M+), 261, 201, 146, 91
$[\alpha]_D^{23} = -182.91°$ (c=1, ethyl acetate)
elemental analysis as C$_{17}$H$_{20}$N$_2$O$_5$S$_2$

|  | C % | H % | N % | S % |
|---|---|---|---|---|
| Calcd. | 51.51 | 5.09 | 7.07 | 16.15 |
| Found | 51.45 | 5.12 | 7.04 | 16.28 |

EXAMPLE 3

33-[(R)-(−)-3-(3-Phenylpropionyl)thiazolidine-4-carbonyl]thiazolidine (Compound H)

To a solution of 2.65 g of (R)-(−)-3-(3-phenylpropionyl)thiazolidine-4-carboxylic acid and 1.15 g of N-hydroxysuccinimide was added a solution of 2.06 g of N,N'-dicyclohexylcarbodiimide with stirring under cooling, and the mixture was allowed to stand overnight under cooling. The precipitates were filtered off, and the filtrate was evaporated under reduced pressure. The residue was dissolved in 15 ml of dimethoxyethane, and to the solution was added 0.89 g of thiazolidine with stirring under ice-cooling. The mixture was allowed to stand overnight, and then evaporated under reduced pressure. To the residue was added 5 ml of water, and the mixture was stirred for 30 minutes. The reaction mixture was extracted with ethyl acetate, and the organic layer was washed successively with a 1N hydrochloric acid, a 5% aqueous sodium bicarbonate solution and a saturated sodium chloride aqueous solution, dried over anhydrous sodium sulfate, and evaporated under reduced pressure. The residue was purified by silica gel column chromatography (eluent:ethyl acetate/benzene=6/4) to obtain 3-[(R)-(−)-(3-phenylpropionyl)-thiazolidine-4-carbonyl]thiazolidine.

melting point: 65°–67° C.
IR (KBr): νco 1660, 1640 cm$^{-1}$
MS(EI): C$_{16}$H$_{20}$O$_2$N$_2$S$_2$=336.3 m/z 336(M+), 247, 203, 143, 105, 88
$[\alpha]_D^{20} = -108.0°$ (c=0.5, ethanol)
elemental analysis as C$_{16}$H$_{20}$N$_2$O$_2$S$_2$

|       | C %   | H %  | N %  | S %   |
|-------|-------|------|------|-------|
| Calcd.| 57.13 | 5.99 | 8.33 | 19.02 |
| Found | 57.39 | 6.18 | 8.23 | 18.56 |

EXAMPLE 4

The following compounds were prepared in a similar manner to that described in Example 3 by using suitable starting materials.

1-[(R)-(−)-3-(3-Phenylpropionyl)thiazolidine-4-carbonyl]pyrrolidine (Compound I)

melting point: 82°–83° C.
IR (KBr): νco 1680, 1640 cm$^{-1}$
MS(EI): $C_{17}H_{22}O_2N_2S$ = 318.38 m/z 318(M+), 247, 185, 126, 105, 88
$[\alpha]_D^{20}$ = −109.6° (c=0.5, dichloromethane)
elemental analysis as $C_{17}H_{22}N_2O_2S$

|       | C %   | H %  | N %  | S %   |
|-------|-------|------|------|-------|
| Calcd.| 64.13 | 6.97 | 8.80 | 10.05 |
| Found | 64.19 | 6.97 | 8.54 | 9.78  |

(R)-(−)-3-[(R)-(−)-3-(3-Phenylpropionyl)-thiazolidine-4-carbonyl]thiazolidine-4-carboxylic acid methyl ester (Compound J)

melting point: 93°–94° C.
IR (KBr): νco 1740, 1660 cm$^{-1}$
MS(EI): $C_{18}H_{22}O_4N_2S_2$ = 394.39 m/z 394(M+), 363, 308, 201, 146, 115, 88
$[\alpha]_D^{20}$ = −185.6° (c=0.5, ethyl acetate)
elemental analysis as $C_{18}H_{22}O_4N_2S_2$

|       | C %   | H %  | N %  | S %   |
|-------|-------|------|------|-------|
| Calcd.| 54.82 | 5.62 | 7.10 | 16.23 |
| Found | 54.98 | 5.64 | 7.03 | 16.10 |

3-[(R)-(−)-3-(4-Phenylbutanoyl)thiazolidine-4-carbonyl]thiazolidine (Compound K)

melting point: 84°–86° C.
IR (KBr): νco 1640 cm$^{-1}$
MS(EI): $C_{17}H_{22}O_2N_2S_2$ = 350.40 m/z 350(M+), 261, 234, 203, 174, 157, 147, 91
elemental analysis as $C_{17}H_{22}O_2N_2S$

|       | C %   | H %  | N %  | S %   |
|-------|-------|------|------|-------|
| Calcd.| 58.27 | 6.33 | 8.00 | 18.27 |
| Found | 58.36 | 6.30 | 8.04 | 18.14 |

1-[(R)-(−)-3-(4-Phenylbutanoyl)thiazolidine-4-carbonyl]pyrrolidine (Compound L)

melting point: 63°–64° C.
IR (KBr): νco 1660, 1638 cm$^{-1}$
MS(EI): $C_{18}H_{24}O_2N_2S$ = 332.41 m/z 332(M+), 207, 185, 147, 126, 91, 70
elemental analysis as $C_{18}H_{24}O_2N_2S$

|       | C %   | H %  | N %  | S %   |
|-------|-------|------|------|-------|
| Calcd.| 65.04 | 7.28 | 8.43 | 9.63  |
| Found | 65.17 | 7.24 | 8.44 | 9.44  |

(R)-(−)-3-[(R)-(−)-3-(4-Phenylbutanoyl)thiazolidine-4-carbonyl]thiazolidine-4-carboxylic acid methyl ester (Compound M)

melting point: 84°–85° C.
IR (KBr): νco 1735, 1660, 1650 cm$^{-1}$
MS(EI): $C_{19}H_{24}O_4N_2S_2$ = 408.40 m/z 408(M+), 377, 361, 201, 147, 115, 91
elemental analysis as $C_{19}H_{24}O_4N_2S_2$

|       | C %   | H %  | N %  | S %   |
|-------|-------|------|------|-------|
| Calcd.| 55.87 | 5.92 | 6.86 | 15.67 |
| Found | 56.27 | 6.00 | 6.98 | 15.42 |

3-[(R)-(−)-3-Phenylacetylthiazolidine-4-carbonyl]thiazolidine (Compound N)

melting point: 127°–129° C.
IR (KBr): νco 1660, 1650 cm$^{-1}$
MS(EI): $C_{15}H_{18}O_2N_2S_2$ = 322.31 m/z 332(M+), 239, 179
$[\alpha]_D^{27}$ = −113.5° (c=1.0, methanol)
elemental analysis as $C_{15}H_{18}O_2N_2S_2$

|       | C %   | H %  | N %  | S %   |
|-------|-------|------|------|-------|
| Calcd.| 55.89 | 5.63 | 8.69 | 18.85 |
| Found | 55.91 | 5.63 | 8.72 | 19.80 |

1-[(R)-(−)-3-Phenylacetylthiazolidine-4-carbonyl]pyrrolidine (Compound O)

melting point: 122°–124° C.
IR (KBr): νco 1650 cm$^{-1}$
MS(EI): $C_{16}H_{20}O_2N_2S$ = 304.32 m/z 304(M+), 206
elemental analysis as $C_{16}H_{20}O_2N_2S$

|       | C %   | H %  | N %  | S %   |
|-------|-------|------|------|-------|
| Calcd.| 63.14 | 6.62 | 9.21 | 10.52 |
| Found | 62.80 | 6.55 | 9.12 | 10.27 |

3-[(R)-(−)-3-Cinnamoylthiazolidine-4-carbonyl]thiazolidine (Compound P)

melting point: 170° C.
IR (KBr): νco 1652, 1640 cm$^{-1}$
MS(EI): $C_{16}H_{18}O_2N_2S_2$ = 334.32 m/z 334(M+), 203, 131, 103
$[\alpha]_D^{27}$ = −101.9°
elemental analysis as $C_{16}H_{18}O_2N_2S_2$

|       | C %   | H %  | N %  | S %   |
|-------|-------|------|------|-------|
| Calcd.| 58.61 | 5.79 | 8.04 | 18.40 |
| Found | 58.56 | 5.77 | 7.89 | 18.41 |

1-[(R)-(−)-3-Cinnamoylthiazolidine-4-carbonyl]pyrrolidine (Compound Q)

melting point: 154°–155° C.
IR (KBr): νco 1650, 1640 cm$^{-1}$

MS(EI): $C_{17}H_{20}O_2N_2S=316.35$ m/z $317(M^++1)$, 227, 255 elemental analysis as $C_{17}H_{20}O_2N_2S$

|  | C % | H % | N % | S % |
|---|---|---|---|---|
| Calcd. | 64.54 | 6.37 | 8.86 | 10.12 |
| Found | 64.61 | 6.56 | 8.87 | 9.74 |

4-[(R)-(−)-3-Cinnamoylthiazolidine-4-carbonyl]thiomorpholine (Compound R)

melting point: 144°–146° C.
IR (KBr): νco 1650 cm$^{-1}$
MS(EI): $C_{17}H_{20}O_2N_2S_2=348.35$ m/z $348(M^+)$, 245, 217, 131, 103
$[\alpha]_D^{20}=-119.16°$ (c=1.0, methanol)
elemental analysis as $C_{17}H_{20}O_2N_2S_2$

|  | C % | H % | N % | S % |
|---|---|---|---|---|
| Calcd. | 58.61 | 5.79 | 8.04 | 18.40 |
| Found | 58.56 | 5.77 | 7.97 | 18.41 |

1-[(R)-(−)-3-(1-Naphthylacetyl)thiazolidine-4-carbonyl]pyrrolidine (Compound S)

IR (neat): νco 1740, 1660 cm$^{-1}$
MS(EI): $C_{20}H_{22}O_2N_2S=354.40$ m/z $354(M^+)$, 283, 168, 141, 126, 115, 88
$[\alpha]_D°=-84.6°$ (c=0.52, ethyl acetate)
elemental analysis as $C_{20}H_{22}O_2N_2S\cdot1/3H_2$

|  | C % | H % | N % | S % |
|---|---|---|---|---|
| Calcd. | 66.65 | 6.19 | 7.77 | 8.88 |
| Found | 66.62 | 6.43 | 7.42 | 8.48 |

3-[(R)-(−)-3-(1-Naphthylacetyl)thiazolidine-4-carbonyl]thiazolidine (Compound T)

IR (neat): νco 1658 cm$^{-1}$
MS(EI): $C_{19}H_{20}O_2N_2S_2=372.39$ m/z $372(M^+)$, 283, 256, 224, 168, 141, 115, 88
$[\alpha]_D°=-82.8°$ (c=0.5, ethyl acetate)
elemental analysis as $C_{19}H_{20}O_2N_2S_2$

|  | C % | H % | N % | S % |
|---|---|---|---|---|
| Calcd. | 61.28 | 5.41 | 7.52 | 17.19 |
| Found | 60.74 | 5.71 | 7.15 | 15.82 |

EXAMPLE 5

3-[(R)-(−)-3-Isonicotinoylthiazoidine-4-carbonyl]thiazolidine (Compound U)

To a solution of a 25% hydrobromic acid in acetic acid was added 1.55 g of 3-[(R)-(−)-3-benzyloxycarbonylthiazolidine-4-carbonyl]thiazolidine, and the mixture was stirred for 2 hours under cooling. The reaction mixture was evaporated under reduced pressure, and the residue was dissolved in 5 ml of water. The solution was washed with diethyl ether, and neutralized with a 4N aqueous sodium hydroxide solution. The mixture was extracted with dichloromethane. The organic layer was washed with a 2% hydrochloric acid methanol solution, dried over anhydrous sodium sulfate, and evaporated under reduced pressure to dryness. The residue was recrystallized from ethyl acetate-methanol to obtain 0.68 g of 3-[(R)-(−)-thiazolidine-4-carbonyl]thiazolidine hydrochloride (yield: 61.4%).

melting point: 174°–180° C.
IR (KBr): νco 1660 cm$^{-1}$
$[\alpha]_D^{15}=-164.3°$ (c=1.0, methanol)
elemental analysis as $C_{17}H_{13}ON_2ClS$

|  | C % | H % | N % | S % |
|---|---|---|---|---|
| Calcd. | 34.91 | 5.44 | 11.64 | 26.63 |
| Found | 34.95 | 5.28 | 11.44 | 26.51 |

To a solution of 0.48 g of 3-[(R)-(−)-thiazolidine-4-carbonyl]thiazolidine hydrochloride and 0.36 g of isonicotinoylchloride hydrochloride in 10 ml of dichloromethane was added 1.6 ml of triethylamine with stirring under cooling. The reaction mixture was stirred for 24 hours at room temperature, and then washed with water, dried over anhydrous sodium sulfate, and evaporated under reduced pressure. The residue was purified by silica gel column chromatography (eluent: chloroform/acetonitrile=1/1) to obtain 0.46 g of 3-[(R)-(−)-3-isonicotinoylthiazolidine-4-carbonyl]thiazolidine (yield: 42%).

melting point: 120°–123° C.
IR (neat): νco 1640 cm$^{-1}$
MS(EI): $C_{13}H_{15}O_2N_3S_2=309.40$ m/z $310(M^+)$
elemental analysis as $C_{13}H_{15}O_2N_3S_2$

|  | C % | H % | N % | S % |
|---|---|---|---|---|
| Calcd. | 50.46 | 4.89 | 13.58 | 20.73 |
| Found | 50.30 | 4.89 | 13.30 | 20.29 |

EXAMPLE 6

Inhibitory Effect for Prolyl Endopeptidase

The inhibitory effect of test compounds for the prolyl endopeptidase was measured by using the enzyme purified from bovine brain according to the method of Yoshimoto et al. [J. Biochem., Vol. 94, pages 1179–1190, (1983)].

[Method of Measurement]

To 0.7 ml of 20 mM of Tris-HCl buffer solution ((pH=7.0) containing 10 mM of EDTA and 10 mM of 2-mercaptoethanol were added 100 μl of prolyl endopeptidase (about 0.14 u/ml) and 100 μl of buffer solution containing $10^{-9}$ to $10^{-4}$ M test compound or 100 μl of the buffer without test compound, as a control group. The mixture was preincubated for 5 minutes at 37° C., and then further incubated for 15 minutes at 37° C. with 100 μl of 5 mM substrate dissolved in 40% dioxane. The enzyme reaction was stopped by adding 1 ml of 25% trichloroacetic acid, and after 5 minutes, the reaction mixture was centrifuged for 10 minutes at 3000 rpm. To 0.5 ml of the supernatant was added 0.5 ml of 0.1% sodium nitrite aqueous solution, and after 3 minutes, 0.5 ml of 0.5% ammonium sulfamate and 1 ml of 0.05% N-(1-naphthyl)ethylenediamine dihydrochloride in ethanol were further added. The mixture was left for 25 minutes at 37° C., and the absorbance was measured at 570 nm.

The enzyme activity at each concentration of the test compounds was calculated by the following equation, and the inhibitory activity of each rest compound was expressed as the concentration which gave a 50% inhibition under the conditions ($IC_{50}$ value).

The unit of the enzyme activity (μmol/min/ml)-
=ΔOD×0.42×a dilution factor

| Compound | Result IC$_{50}$ value |
|---|---|
| A | 0.26 nM |
| B | 72 μM |
| C | 160 μM |
| F | 0.23 mM |
| G | 0.21 μM |
| H | 0.4 μM |
| N | 63.1 nM |
| O | 0.66 μM |
| P | 3.24 μM |
| Q | 4.6 μM |
| U | 1.3 μM |

What is claimed is:

1. A thiazolidine compound corresponding to the formula:

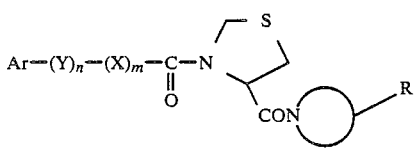

where Ar is a phenyl, naphthyl or pyridyl group; Y is a saturated or olefinically unsaturated alkylene group having 1–5 carbon atoms; n is an integer with a value of zero or 1;

is a 5- or 6-membered saturated heterocyclic group; X is an oxygen atom; m is an integer with a value of zero or 1;

R is hydrogen or an alkoxycarbonyl group having 2–6 carbon atoms; and pharmaceutically acceptable salts thereof.

2. A thiazolidine compound corresponding to the formula:

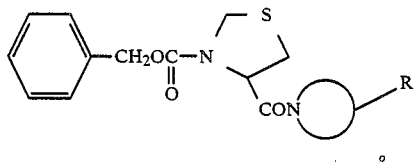

where

is a 5- or 6-membered saturated heterocyclic group; and R is or an alkoxycarbonyl group having 2–6 carbon atom.

3. 3-[(R-(—)-3-Benzyloxycarbonylthiazolidine-4-carbonyl]thiazolidine.

4. (S)-(—)-N-[(R)-(—)-3-Benzyloxycarbonylthiazolidine-4-carbonyl]pyrrolidine-2-carboxylic acid methyl ester.

5. N-[(R)-(—)-3-Benzyloxycarbonylthiazolidine-4-carbonyl]thiazolidine.

6. N-[(R)-(—)-3-Benzyloxycarbonylthiazolidine-4-carbonyl]piperidine.

7. N-[(R)-(—)-3-Benzyloxycarbonylthiazolidine-4-carbonyl]morpholine.

8. N-[(R)-(—)-3-Benzyloxycarbonylthiazolidine-4-carbonyl]thiomorpholine.

9. (R)-(—)-3-[(R)-(—)-Benzyloxycarbonylthiazolidine-4-carbonyl]thiazolidine-4-carboxylic acid methyl ester.

10. 3-[(R)-(—)-3-(3-Phenylpropionyl)thiazolidine-4-carbonyl]thiazolidine.

11. 1-[(R)-(—)-3-Phenylpropionyl)thiazolidine-4-carbonyl]pyrrolidine.

12. (R)-(—)-3-[(R)-(—)-3-(3-Phenylpropionyl)-thiazolidine-4-carbonyl]thiazolidine-4-carboxylic acid methyl ester.

13. 3-[(R)-(—)-3-(4-Phenylbutanoyl)thiazolidine-4-carbonyl]thiazolidine.

14. 1-[(R)-(—)-3-(4-Phenylbutanoyl)thiazolidine-4-carbonyl]pyrrolidine.

15. (R)-(—)-3-[(R)-(—)-3-(4-Phenylbutanoyl)thiazolidine-4-carbonyl]thiazolidine-4-carboxylic acid methyl ester.

16. 3-[(R)-(—)-3-Phenylacetylthiazolidine-4-carbonyl]thiazolidine.

17. 1-[(R)-(—)-3-Phenylacetylthiazolidine-4-carbonyl]pyrrolidine.

18. 3-[(R)-(—)-3-Cinnamoylthiazolidine-4-carbonyl]thiazolidine.

19. 1-[(R)-(—)-3-Cinnamoylthiazolidine-4-carbonyl]pyrrolidine.

20. 4-[(R)-(—)-3-Cinnamoylthiazolidine-4-carbonyl]thiomorpholine.

21. 1-[(R)-(—)-3-(1-Naphthylacetyl)thiazolidine-4-carbonyl]pyrrolidine.

22. 3-[(R)-(—)-3-(-Naphthylacetyl)thiazolidine-4-carbonyl]thiazolidine.

23. 3-[(R)-(—)-Isonicotinoylthiazolidine-4-carbonyl]thiazolidine.

24. A method of treatment for dementia or amnesia which comprises administering a prescribed dosage to a human patient of a therapeutic agent corresponding to the formula:

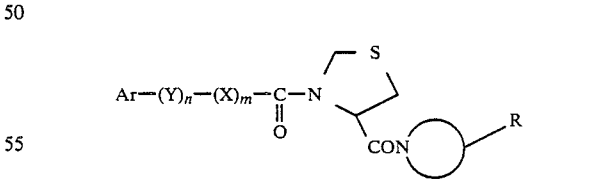

wherein Ar is a phenyl, naphthyl or pyridyl group; Y is a saturated or olefinically unsaturated alkylene group having 1–5 carbon atoms; n is an integer with a value of zero or 1;

is a 5- or 6-membered saturated heterocyclic group; X is an oxygen atom; m is an integer with a value of zero or 1; R is hydrogen or an alkoxycarbonyl group having 2-6 carbon atoms; or pharmaceutically acceptable salt thereof.

25. A method of treatment in accordance with claim 24 wherein the therapeutic agent corresponds to the formula:

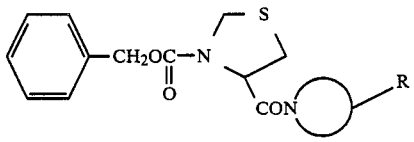

where

and R are previously defined.

26. A method of treatment in accordance with claim 24 wherein the prescribed dosage of therapeutic agent is in the range from about 50 mg to 1000 mg for an adult human by oral administration per day, or from about 1 mg to 500 mg for an adult human by parenteral administration per day.

27. A method of treatment for dementia or amnesia which comprises administering a prescribed dosage to a human patient of a therapeutic agent selected from any one of the compounds defined in claims 3-23.

* * * * *

UNITED STATES PATENT OFFICE
CERTIFICATE OF CORRECTION

Patent No. 4,857,524  Dated 8/15/89

Inventor(s) Furukawa et al

It is certified that error appears in the above-identified patent and that said Letters Patent is hereby corrected as shown below:

Col. 1, line 15, in the formula, line from R should go into circle.

Col. 3, line 45, in the formula, put line from R into circle.
Col. 5, line 35, in the formula, put line from R into circle.
Col. 10, line 38, "33" should be --3--.

Col. 13, line 30, "$[\alpha]_{D°}$" should be --$[\alpha]_D$ --.

Col. 13, line 44, "$[\alpha]_{D°}$" should be --$[\alpha]_D$ --

Col. 14, line 66, "rest" should be --test--.

Col. 15, line 25, in the formula, put line from R into circle.

Col. 15, line 50, in the formula, put line from R into circle.

Col. 16, line 55, in the formula, put line from R into circle.

UNITED STATES PATENT AND TRADEMARK OFFICE
CERTIFICATE OF CORRECTION

PATENT NO. : 4,857,524

DATED : 8/15/89

INVENTOR(S) : Furukawa et al.

It is certified that error appears in the above-identified patent and that said Letters Patent is hereby corrected as shown below:

Col. 17, line 15, in the formula, put line from R into circle.

Signed and Sealed this

Eleventh Day of December, 1990

Attest:

HARRY F. MANBECK, JR.

*Attesting Officer*  *Commissioner of Patents and Trademarks*